US00PP19920P2

(12) United States Plant Patent
Zaiger et al.

(10) Patent No.: US PP19,920 P2
(45) Date of Patent: Apr. 14, 2009

(54) CHERRY TREE NAMED 'ROYAL HAZEL'

(50) Latin Name: *Prunus avium*
Varietal Denomination: Royal Hazel

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 12/003,505

(22) Filed: Dec. 26, 2007

(51) Int. Cl.
*A01H 5/00* (2006.01)

(52) U.S. Cl. ..... Plt./181

(58) Field of Classification Search ..... Plt./181
See application file for complete search history.

*Primary Examiner*—Annette H Para
*Assistant Examiner*—June Hwu

(57) ABSTRACT

A new and distinct variety of cherry tree. The following features of the tree and its fruit are characterized with the tree budded on 'Mahaleb' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. A low chilling requirement of approximately 500 hours at or below 45° F.
2. Fruit maturing in the early season.
3. Fruit with an attractive red skin color.
4. Fruit with very good flavor and eating quality.
5. The ability of the fruit to remain firm on the tree 7 days past maturity.
6. Heavy and regular production of large size fruit.

1 Drawing Sheet

Botanical classification: *Prunus avium.*

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of cherry tree was originated and asexually reproduced by us in our experimental orchard located near Modesto, Stanislaus County, Calif.

Prior Varieties

Among the existing varieties of cherry trees, which are known to us, and mentioned herein, 'Bing' Cherry (non-patented) and 'Minnie Royal' Cherry (U.S. Plant Pat. No. 12,942).

Origin of the Variety

The present new variety of cherry tree (*Prunus avium*) was originated by us in our experimental orchard located near Modesto, Calif. as an open pollinated seedling from a proprietary seedling selection with the field identification number '25Z116'. The selection '25Z116' originated from a first generation cross between two selected proprietary seedlings. The two proprietary seedlings originated from a cross of a selected seedling of 'Bing' Cherry (non-patented) and a low chilling cherry seedling of unknown parentage. A large group of these open pollinated seedlings were budded on established 'Mahaleb' Rootstock (non-patented) to accelerate fruit production and maintained under close and careful observation, one such low chilling seedling, which is the present variety, bearing heavy production of large size, early maturing fruit with very good eating quality, was selected in 2002 for asexual reproduction and commercialization.

Asexual Reproduction of the Variety

Additional asexual reproduction of the new and distinct variety of cherry tree was by budding to 'Mahaleb' Rootstock (non-patented), as performed by us in our experimental orchard located near Modesto, Calif., and shows that reproductions run true to the original tree and all characteristics of the tree and its fruit are established and transmitted through succeeding asexual reproductions.

SUMMARY OF THE NEW VARIETY

The new and distinct cherry tree is of large size, vigorous upright growth and has a low winter chilling requirement of approximately 500 hours at or below 45° F. The tree is a regular and productive bearer of early maturing, large size, firm fruit with very good flavor and eating quality. The fruit is further characterized by its attractive red skin color and its ability to remain firm on the tree 7 days past maturity (shipping ripe). In comparison to its ancestor 'Bing' Cherry (non-patented) the new variety has a lower winter chilling requirement, blooming approximately 10 days earlier, having a wider range of adaptability, and fruit that matures approximately 12 days earlier. In comparison to its seed parent (25Z116) the new variety blooms approximately 10 days earlier, has firmer fruit with more distinct flavor and matures approximately 12 days earlier. In comparison to 'Minnie Royal' (U.S. Plant Pat. No. 12,942) the new variety has the same low winter chilling requirement of 500 hours at or below 45° F. and approximately 8 days later in maturity.

PHOTOGRAPH OF THE VARIETY

The accompanying color photographic illustration shows typical specimens of the foliage and fruit of the present new cherry variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 9 year old tree and the colors are as nearly true as is reasonably possible in a color representation of this type.

DESCRIPTION OF THE VARIETY

The following is a detailed botanical description of the new variety of cherry tree, its flowers, foliage and fruit, as based on observations of 9 year old specimens grown near Modesto, Calif., with color in accordance with Munsell Book of Color.

Tree:

*Size.*—Large. Tree pruned to 3 to 4 meters in height and 2 to 3 meters in width for economical harvesting of fruit.

*Vigor.*—Vigorous. Tree growth reaching 1 to 2 meters the first growing season. Growth rate will vary slightly with soil type and depth, cultural practices and climatic conditions.

*Form.*—Upright. During the first and second growing seasons scaffolds are selected and tied down to increase crotch angle and help spread to desired width.

*Branching habit.*—Upright. Crotch angle approximately 30°, heavy fruit production tends to increase the branch angles.

*Productivity.*—Productive, produces a heavy crop annually.

*Bearer.*—Regular, adequate fruit set for 6 consecutive years.

*Fertility.*—Self sterile, pollinator required.

*Density.*—Medium dense. Usually pruned to vase shape to enhance health of fruit spurs by allowing greater air movement and sunshine.

*Hardiness.*—Hardy in all stone fruit growing areas of California. Tree grown in USDA Hardiness Zone 9. Winter chilling requirement is approximately 500 hours at or below 45° F.

Trunk:

*Size.*—Large. Measured 46.9 cm in circumference at 30.5 cm above ground on a 9 year old tree.

*Stocky.*—Medium stocky.

*Texture.*—Medium rough, varies with age of growth.

*Color.*—Varies from 10YR 5/2 to 10YR 3/2.

Branches:

*Size.*—Medium. Average circumference 14.7 cm at 1.2 meters above ground.

*Surface texture.*—Smooth on new growth, becomes medium rough on mature growth.

*Lenticels.*—Numerous. Averages 28 in a 25.8 sq cm section. Average length 3.8 mm. Average width 2.2 mm. Color varies from 7.5YR 5/8 to 10YR 5/8.

*Color.*—New growth varies from 2.5GY 6/6 to 5GY 5/8. Old growth varies from 10YR 5/2 to 10YR 3/6, varies with age of growth.

Leaves:

*Size.*—Large. Average length 131.0 mm. Average width 59.3 mm.

*Form.*—Lanceolate.

*Apex.*—Acuminate.

*Base.*—Cuneate.

*Margin.*—Doubly serrate.

*Thickness.*—Medium.

*Surface texture.*—Upper surface relatively smooth, slight indentations over leaf veins, glabrous. Lower surface relatively smooth, slight ridges created by midrib and pinnate venation, glabrous.

*Petiole.*—Average length 37.2 mm. Average width 1.9 mm. Grooved longitudinally. Color varies from 2.5GY 5/8 to 7.5R 3/6 where exposed to the sun. Surface — glabrous.

*Glands.*—Reniform. Large size. Number varies from 1 to 3, average number 2. Average length 1.6 mm. Average width 1.2 mm. Located primarily on the upper portion of petiole. Color varies from 7.5R 3/12 to 7.5R 2/8.

*Color.*—Upper surface varies from 7.5GY 4/8 to 5GY 3/6. Lower surface varies from 5GY 4/4 to 5GY 4/6. Midvein color varies from 2.5GY 7/8 to 2.5GY 5/8.

Flower buds:

*Size.*—Large. Average length 18.8 mm. Average diameter 11.0 mm.

*Hardiness.*—Hardy with respect to California winters.

*Form.*—Plump, conical.

*Pedicel.*—Average length 14.7 mm. Average width 1.3 mm. Color varies from 2.5GY 6/6 to 5GY 5/8.

*Color.*—N 9.5/ (white).

*Number of buds per spur.*—Average 7, varies from 5 to 12.

Flowers:

*Size.*—Large. Average height 19.4 mm. Average diameter 33.8 mm.

*Petals.*—Number 5, alternately arranged to sepals. Nearly orbicular, narrows at point of attachment. Margin — sinuate with slight cleft at center of apex. Average length 18.1 mm. Average width 17.4 mm. Both upper and lower surfaces glabrous. Color — N 9.5/ (white).

*Sepals.*—Number 5, alternately arranged to petals. Triangular shape. Both upper and lower surfaces glabrous. Average length 8.1 mm. Average width 5.5 mm. Color — upper surface varies from 5GY 5/8 to 5GY 4/6. Lower surface varies from 5GY 5/6 to 5R 3/6.

*Stamens.*—Average number per flower 38. Average filament length 12.5 mm. Filament color N 9.5/ (white). Anther color varies from 5Y 8/8 to 5Y 8/10.

*Pollen.*—Self sterile, pollinator required. Color varies from 5Y 7/10 to 5Y 7/12.

*Pistil.*—Normally one. Average length 15.9 mm. Position of stigma average of 1.2 mm above anthers. Surface — glabrous. Color varies from 2.5GY 8/6 to 2.5GY 7/8.

*Fragrance.*—Slight.

*Blooming period.*—Data of First Bloom Mar. 6, 2007. Date of Petal Fall Mar. 16, 2007, varies slightly with climatic conditions.

*Color.*—N 9.5/ (white).

*Number of flowers per flower bud.*—Average 4, varies from 1 to 6.

*Pedicel.*—Average length 15.8 mm. Average width 1.4 mm. Color varies from 5GY 6/6 to 5GY 5/6.

Fruit:

*Maturity when described.*—Firm ripe.

*Date of first picking.*—May 9, 2007.

*Date of last picking.*—May 16, 2007, varies slightly with climatic conditions.

*Size.*—Large. Average diameter axially 25.6 mm. Average transversely in suture plane 26.5 mm. Average weight 12.6 grams, varies with fertility of the soil, amount of thinning and climatic conditions.

*Form.*—Globose, slightly flattened at apex and base.

*Suture.*—Relatively smooth, extends from base to apex.

*Ventral surface.*—Smooth, nearly rounded.

*Apex.*—Varies from slightly retuse to rounded.

*Base.*—Flat to slightly retuse.

*Cavity.*—Rounded. Average depth 1.0 mm. Average diameter 2.7 mm.

Stem:

*Size.*—Small to medium. Average length 30.2 mm. Average diameter 1.6 mm.

*Color.*—Varies from 5GY 5/6 to 5GY 4/6.

Flesh:

*Ripens.*—Evenly.

*Texture.*—Firm, meaty.

*Fibers.*—Few, small, tender.

*Aroma.*—Slight.

*Amydgalin.*—Undetected.

*Eating quality.*—Very good.

*Flavor.*—Very good, good balance between acid and sugar.

*Juice.*—Very juicy, enhances flavor.

*Brix.*—Average Brix 16.3°, varies slightly with amount of fruit per tree and climatic conditions.

*Color.*—Varies from 5R 3/8 to 7.5R 2/8, varies with fruit maturity. Pit cavity varies from 5R 2/4 to 7.5R 2/4.

Skin:

*Thickness.*—Medium.

*Surface.*—Smooth.

*Bloom.*—Wanting.

*Tendency to crack.*—None during dry weather, only slight tendency to crack in wet weather. Depends on stage of maturity.

*Color.*—Varies from 7.5R 3/10 to 7.5R 2/8.

*Tenacity.*—Tenacious to flesh.

*Astringency.*—None.

Stone:

*Type.*—Clingstone.

*Size.*—Small to medium. Average length 10.3 mm. Average width 8.8 mm. Average thickness 7.0 mm.

*Form.*—Obovoid.

*Base.*—Flat.

*Apex.*—Rounded.

*Surface.*—Relatively smooth throughout.

*Sides.*—Equal to unequal. Some stones have one side extending further from suture plane.

*Ridges.*—A small narrow ridge on each side of the suture, extending from base to apex.

*Tendency to split.*—None.

*Color.*—Varies from 7.5YR 6/6 to 10YR 6/6 when dry.

Kernel:

*Form.*—Ovoid.

*Taste.*—Bitter.

*Viability.*—Viable, good embryo development.

*Size.*—Small to medium. Average length 7.7 mm. Average width 5.4 mm. Average depth 4.7 mm.

*Skin color.*—Varies from 5Y 9/2 to 5Y 9/4.

Use: Dessert. Market — local and long distance.

Keeping quality: Good, held firm for 14 days in cold storage at 38° to 42° F. and maintained good appearance and eating quality.

Shipping quality: Good, minimal flesh bruising or skin scarring during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

What is claimed is:

1. A new and distinct variety of cherry tree, substantially as illustrated and described, characterized by its large size, vigorous, upright growth and being a regular and productive bearer of early maturing, large size fruit that have the ability to remain firm on the tree 7 days past maturity (shipping ripe); the fruit is further characterized by its attractive red skin color, very good flavor and eating quality, and in comparison to 'Bing' Cherry (non-patented), the new variety blooms approximately 10 days earlier and the fruit matures approximately 12 days earlier.

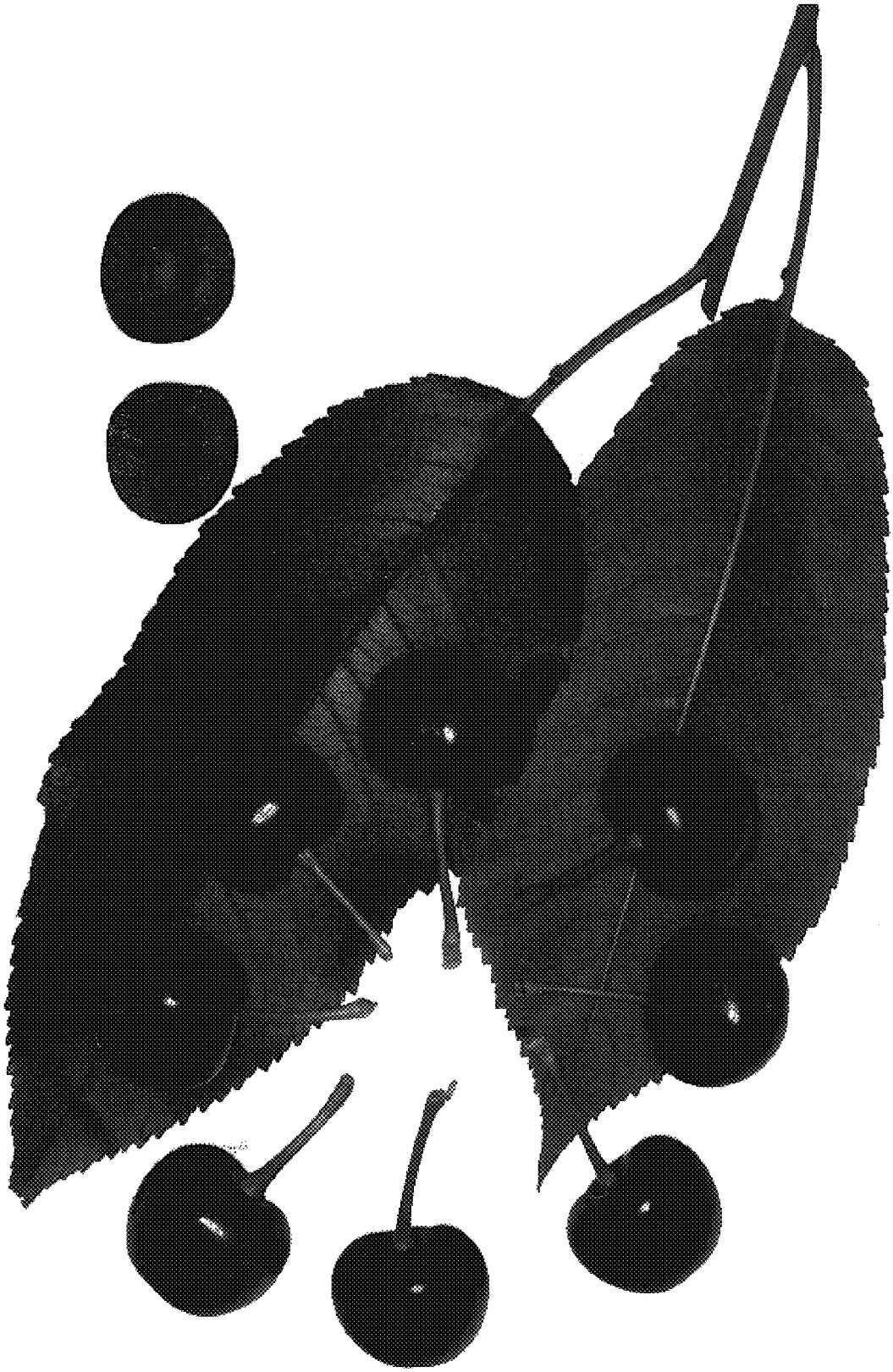

* * * * *